US00RE48970E

(19) United States
(12) Reissued Patent
Toumazou et al.

(10) Patent Number: US RE48,970 E
(45) Date of Reissued Patent: Mar. 15, 2022

(54) IMPLANTABLE SURFACE ACOUSTIC WAVE DEVICES FOR LONG TERM CLINICAL MONITORING

(71) Applicant: IP2IPO INNOVATIONS LIMITED, London (GB)

(72) Inventors: Christofer Toumazou, London (GB); Christopher Neil McLeod, Headington (GB); Glenn Noel Robert Vandevoorde, Parkshore (SG)

(73) Assignee: IP2IPO INNOVATIONS LIMITED, London (GB)

(21) Appl. No.: 16/576,358

(22) Filed: Sep. 19, 2019

Related U.S. Patent Documents

Reissue of:
(64) Patent No.: 8,764,677
Issued: Jul. 1, 2014
Appl. No.: 10/582,482
PCT Filed: Dec. 14, 2004
PCT No.: PCT/GB2004/005228
§ 371 (c)(1),
(2) Date: Jun. 14, 2007
PCT Pub. No.: WO2005/058166
PCT Pub. Date: Jun. 30, 2005

U.S. Applications:
(62) Division of application No. 15/200,799, filed on Jul. 1, 2016, now Pat. No. Re. 47,681, which is an application for the reissue of Pat. No. 8,764,677.

(30) Foreign Application Priority Data

Dec. 15, 2003 (GB) ..... 0329019

(51) Int. Cl.
*A61B 5/00* (2006.01)
*A61B 8/00* (2006.01)
(Continued)

(52) U.S. Cl.
CPC ..... *A61B 5/0031* (2013.01); *A61B 5/0215* (2013.01); *A61B 5/031* (2013.01); *A61B 8/04* (2013.01); *A61B 8/4472* (2013.01)

(58) Field of Classification Search
CPC ..... A61B 5/0031; A61B 8/4472; A61B 8/04; A61B 5/0125; A61B 5/031
(Continued)

(56) References Cited

U.S. PATENT DOCUMENTS 4,265,124 A * 5/1981 Lim et al. ..... 73/703
4,454,440 A 6/1984 Cullen
(Continued)

FOREIGN PATENT DOCUMENTS

GB 2376362 A 12/2002
JP 550040967 A 3/1980
(Continued)

OTHER PUBLICATIONS

B. Jakoby, H. Eisenschmid, F. Hermann, "The Potential of Microacoustic SAW-and BAW-based Sensors for Automotive Applications—a Review." Sensors Journal, Oct. 2002, vol. 2, Issue: 5, pp. 443-452.
(Continued)

*Primary Examiner* — Beverly M Flanagan
(74) *Attorney, Agent, or Firm* — Maine Cernota & Rardin

(57) ABSTRACT

A surface or bulk acoustic wave device can be implanted in or worn on a human or animal body to monitor various parameters thereof. The device comprises a pair of interdigitated transducers spaced apart over the surface of a piezo-electric substrate that is exposed to the parameter to be monitored. The device is interrogated by a radio-frequency signal being supplied to one of the transducers and detected after reflection by the other transducer. The parameter is measured by comparison of the supplied and received signals.

6 Claims, 1 Drawing Sheet

(51) Int. Cl.
*A61B 8/04* (2006.01)
*A61B 5/03* (2006.01)
*A61B 5/0215* (2006.01)

(58) Field of Classification Search
USPC ..... 600/481, 486, 488, 561
See application file for complete search history.

(56) References Cited

U.S. PATENT DOCUMENTS

| | | | | | |
|---|---|---|---|---|---|
| 4,535,631 | A | * | 8/1985 | Sinha et al. | 73/703 |
| 4,622,855 | A | * | 11/1986 | Sinha et al. | 73/703 |
| 4,691,714 | A | | 9/1987 | Wong et al. | |
| 4,705,979 | A | * | 11/1987 | Sinha | 310/313 A |
| 4,773,428 | A | | 9/1988 | Wong et al. | |
| 5,129,262 | A | * | 7/1992 | White et al. | 73/599 |
| 5,189,914 | A | * | 3/1993 | White et al. | 73/599 |
| 5,700,952 | A | | 12/1997 | Andersen | |
| 5,702,431 | A | | 12/1997 | Wang et al. | |
| 5,938,612 | A | | 8/1999 | Kline-Schoder et al. | |
| 6,206,835 | B1 | | 3/2001 | Spillman, Jr. et al. | |
| 6,330,885 | B1 | * | 12/2001 | Weissman et al. | 128/899 |
| 6,393,921 | B1 | * | 5/2002 | Grimes et al. | 73/728 |
| 6,398,734 | B1 | | 6/2002 | Cimochowski et al. | |
| 6,539,253 | B2 | | 3/2003 | Thompson et al. | |
| 6,767,327 | B1 | * | 7/2004 | Corl et al. | 600/486 |
| 7,017,404 | B1 | * | 3/2006 | Kain | 73/146.5 |
| 2004/0020299 | A1 | * | 2/2004 | Freakes et al. | 73/702 |
| 2004/0039264 | A1 | * | 2/2004 | Bardy | 600/300 |
| 2004/0260346 | A1 | * | 12/2004 | Overall et al. | 607/4 |

FOREIGN PATENT DOCUMENTS

| | | | | |
|---|---|---|---|---|
| JP | 559098323 | A | 7/1980 | |
| JP | SHO55-098323 | | 7/1980 | |
| JP | 55164324 | | 12/1980 | |
| JP | 60195546 | A | 10/1985 | |
| JP | 60-195546 | | 12/1985 | |
| JP | 01253627 | | 9/1989 | |
| JP | 01-253627 | | 10/1989 | |
| JP | 070012654 | A | 1/1995 | |
| JP | 010119728 | A | 5/1998 | |
| JP | 2001190507 | | 7/2001 | |
| JP | 2003144417 | | 5/2003 | |
| JP | 2003319911 | A | 11/2003 | |
| WO | WO 9829030 | A1 * | 7/1998 | A61B 5/02 |
| WO | 0231461 | A1 | 4/2002 | |

OTHER PUBLICATIONS

International Search Report and Written Opinion for PCT Appl. No. PCT/GB2004/005228, dated Mar. 30, 2005, 10 Pages.

International Preliminary Report on Patentability for PCT Appl. No. PCT/GB2004/005228, dated Jun. 20, 2006, 7 Pages.

Das et al. "A pressure Sensing acoustic surface wave resonator," 1976 Ultrasonics Symposium Proceedings, IEEE Cat. No. 76 Ch1120-5SU.*

Das et al, "A self-transmitting surface acoustic wave (SAW) pressure transducer" Journal of Bioengineering vol. 2, pp. 27-32, 1978.*

A Wireless AQP Pressure Sensor Using Chirped SAW Delay Lines Structures L. Reindl, C.C.W. Ruppel, K. Riek, T. Pankratz*, and R. Weigel' Siemens AG, IEEE Ultrasonics Symposium 1998.*

E. Benes, M. Groschl, F. Seifert, A. Pohl, Comparison Between BAW and SAW Sensor principles, Frequency Control Symposium, 1997., Proceedings of the 1997 IEEE International, May 28, 1997, pp. 5-20.

* cited by examiner

IMPLANTABLE SURFACE ACOUSTIC WAVE DEVICES FOR LONG TERM CLINICAL MONITORING

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATIONS

*More than one reissue application has been filed for the reissue of U.S. Pat. No. 8,764,677; the reissue applications are the present application and application Ser. No. 15/200,799. This application is also a reissue divisional of application Ser. No. 15/200,799, which is an application for reissue of U.S. Pat. No. 8,764,677.* This application is a national phase of International Application No. PCT/GB2004/005228, filed Dec. 14, 2004, and claiming priority to Great Britain Application No. 0329019.4, filed Dec. 15, 2003, the entire contents of which are incorporated herein by reference.

The present invention relates to acoustic wave devices, and particularly, though not exclusively to Surface Acoustic Wave (SAW) devices. SAW devices have been known for nearly two decades with their main applications being in signal processing for telecommunications and more recently as remote sensors in the automotive industry. Their main advantages are their ability a) to act as transducers for physical and chemical measurements, b) to implement complex signal processing functions on a small piezo-electric substrate in a completely passive way, and c) to communicate with remote electronic systems using electromagnetic waves.

The present invention is concerned, in one aspect, with the use of SAW devices for implantable (internal to the body) or wearable (external to the body, and not necessarily in direct contact therewith) physiological monitoring.

The object of physiological monitoring design is to produce a system which allows continuous, real-time, long term, accurate monitoring of a variety of variables in a safe and clinically acceptable way. Numerous attempts have been made to achieve this object but in practice these attempts have fallen significantly short of successfully achieving many aspects of the ideal due to the large size, the need for electrical power (limited by available battery life), lack of accuracy, infection risk and performance degradation of such devices.

In routine healthcare it is often desirable to measure some parameters which will indicate some aspects of the patient's state of health. With many measurements there is an infinitesimally low risk so that there is no question about the value of making the measurement. With many other measurements, however, there is an associated risk and the clinical technician uses judgment and experience to decide whether or not to make those measurements. Measuring signals that are localised within the body usually involves balancing the value of the measurement against the risk associated with an invasive procedure.

As an example, blood pressure measurement can be achieved in a number of ways, which are here presented in order of increasing risk:

1. Measurement of a representative systemic blood pressure can be achieved indirectly using an external inflatable cuff on the forearm.
2. Measurement of systemic blood pressure more accurately involves penetrating to an artery and inserting a catheter (cannula).
3. Measurement of left ventricular pressure involves inserting a catheter in an artery and advancing it until the tip is in the left ventricle.

For long-term monitoring of patients the repeated use of invasive measurements increases the risk and can ultimately lead to the physician deciding that such a procedure is too risky to undertake.

Implantable sensors offer an alternative to the problems of existing blood pressure measurement techniques set out above, for example. Once implanted, they can provide information over a long period without further risk each time they are used.

Communication with the implant can be achieved through inductive coupling or through a radio-frequency link from a transmitter/receiver located outside the patient's body. U.S. Pat. No. 6,206,835 describes the use of SAW device whose characteristic impedance is altered by a variable-capacitor type of pressure transducer which loads the SAW. Another approach is disclosed in U.S. Pat. No. 5,702,431, in which an implanted battery-powered circuit is recharged using inductive coupling. U.S. Pat. No. 6,539,253 describes the use of SAW filters in implants; the great stability and high Q-factor of the SAW devices are said to be advantageous in the design of the electronics.

Whilst surface acoustic wave devices are preferred for the applications envisages, bulk acoustic wave devices may alternatively by required for more electrical power.

In accordance with one aspect of the present invention, an implantable, or wearable, surface, monitoring parameters, such as pressure, temperature, viscosity, or flow rate within a human or animal body.

In accordance with another aspect of the present invention, there is provided a method of monitoring a parameter of a human or animal body wherein a surface acoustic wave device is implanted therein or attached thereto, wherein the device comprises a pair of interdigitated transducers spaced apart over the surface of a piezo-electric substrate, that is exposed to the parameter, wherein an antenna is connected to one of the interdigitated transducers, wherein a radio-frequency signal is supplied externally of the body to the antenna, is transmitted over the substrate surface to the other of the transducers, reflected therefrom back to the said one of the transducers and transmitted from the antenna thereof to a receiver, whereby comparison of the supplied and received signal provides a measurement of the parameter.

In accordance with a further aspect of the present invention, there is provided a method of monitoring a parameter of a number or animal body wherein a surface acoustic wave device is implanted therein or attached thereto, wherein the device comprises a pair of interdigitated transducers spaced apart over the surface of a piezo-electric substrate that is exposed to the parameter, wherein a respective antenna is connected to each of the interdigitated transducers, wherein a radio-frequency signal is supplied externally of the body selectively to one of the antennae, is transmitted over the surface of the substrate the associated transducer to the other transducer and is transmitted from the other of the antennae to a receiver, whereby comparison of the supplied and received signal provides a measurement of the parameter.

In accordance with yet another aspect of the present invention, there is provided a method of monitoring a parameter of a human or animal body wherein a bulk acoustic wave device is implanted therein or attached thereto, wherein the device comprises a pair of interdigitated transducers spaced apart over the surface of a piezoelectric substrate, that is exposed to the parameter, wherein a radio-frequency signal is supplied externally of the body to the antenna, is transmitted over the substrate surface to the other of the transducers, reflected therefrom back to the said one of the transducers and transmitted from the antenna thereof to a receiver, whereby comparison of the supplied and received signals provides a measurement of the parameter.

In accordance with yet another aspect of the present invention, there is provided a method of monitoring a parameter of a human or animal body wherein a bulk acoustic wave device is implanted therein or attached thereto, wherein the device comprises a pair of interdigitated transducers spaced apart over the surface of a piezo-electric substrate that is exposed to the parameter, wherein a respective antenna is connected to each of the interdigitated transducers, wherein a radio-frequency signal is supplied externally of the body selectively to one of the antennae, is transmitted over the surface of the substrate form the associated transducer to the transducer and is transmitted from the other of the antennae to a receiver whereby comparison of the supplied and received signals provides a measurement of the parameter.

The body's parameter may be monitored by determination of a delay or a change of resonant frequency of the acoustic wave.

A plurality of acoustic wave devices may be employed being arranged to operate at different frequencies for differentiation therebetween.

SAW devices have been found to be particularly advantageous for such applications because of their sensitivity to physical or chemical variables, very small size, inherent stability and zero in-situ power requirement. This results in a significant change in the quality and quantity of information made available to clinicians with minimal risk to the patient. SAW devices may also be used as the communication link to and from other implanted systems or devices.

Thus, the present invention relates, for example, to medical implant devices—used as sensors—which can be interrogated from outside the body without physical connection thereto. The signals received from the sensor contain information relating to the patient's medical condition which can subsequently be used for diagnostic purposes and/or for the automatic control or an applied device or therapy.

This invention relates to the use of SAW devices acting as both the sensing element for the required measurement and the communication element for the remote acquisition of the measurement.

Applications of the present invention for the use of SAW devices for measuring pressure, and will now be described by way of example, with reference to the accompanying drawings, in which.

One of the most demanding and critical tasks in physiological monitoring is the assessment of the ongoing condition of the heart and major blood vessels. Currently, the only information the cardiac or cardiovascular surgeon has is either indirect or it results from one-off invasive—and therefore risky—measurements, leaving the surgeon with relatively little feedback on the success of the applied therapy. Minimally invasive transponders to monitor local cardiac, arterial or venous pressure in accordance with the present invention result in a significant step forward. The transponders can be implanted within the heart chambers or elsewhere in the cardiovascular system to monitor local pressure for measuring absolute or differential pressures throughout the system.

Two possible approaches are:

1) use as a delay line: pressure is related to the time taken for the SAW to travel over the surface of the device.
2) use as a resonator: pressure alters the natural frequency of the device.

Use as a Delay Line

The monitoring system comprises an implantable transponder 2 made up of a SAW device (FIG. 1) and an antenna 4.

Figure 1:
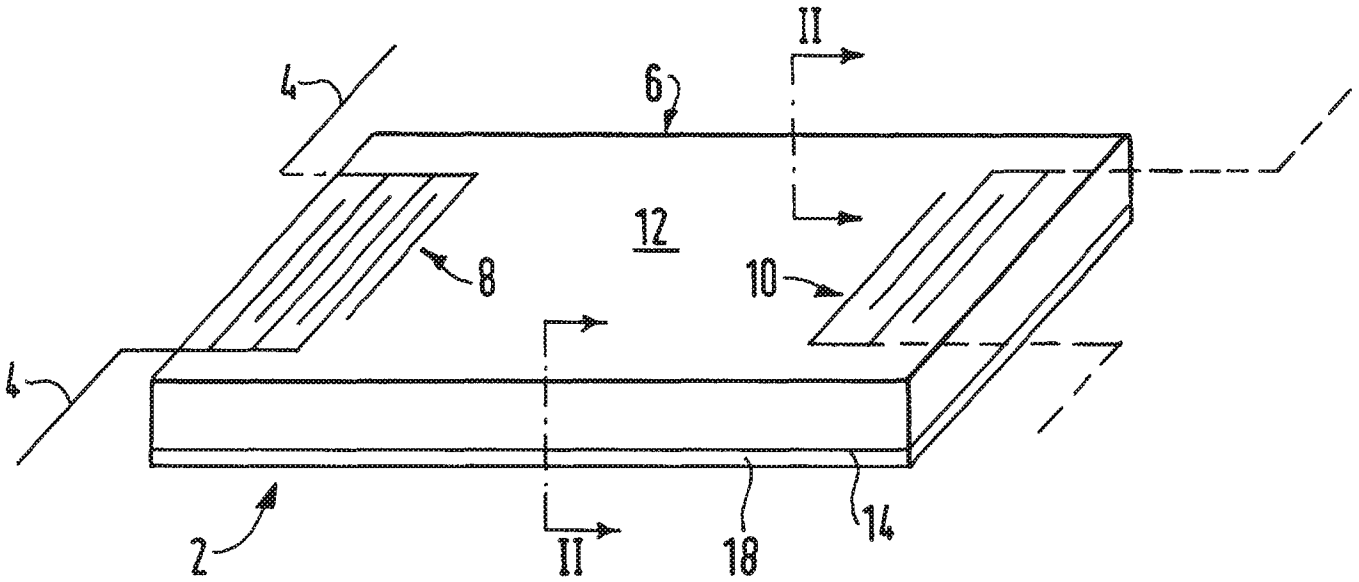
FIG 1 is a schematic isometric view of one SAW device.
Figure 2:
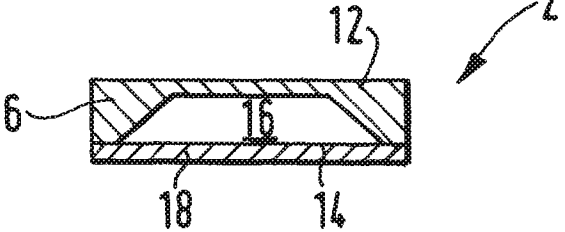
FIG. 2 is a section of the line II-II of FIG. 1.

The SAW device 2 is made pressure sensitive by forming it on an under-etched substrate sealed over a reference chamber that is filled with a vacuum or pressurised gas. Referring to FIG. 1, the SAW device transponder 2 comprises a generally rectilinear body 6 of piezo-electric material. Two sets of metal interdigital fingers (IDTs) 8, 10 are deposited spaced apart on one major, upper, surface 12 of the body 6. As shown, an antenna 4 is connected to one IDT 8, and no antenna is connected the other IDT 10. The other, lower, major surface 14 of the transducer body 6 is etched away to form a chamber 16 that is closed by a sealing layer 18. The chamber 16 may be evacuated or filled with a pressurised gas at a reference pressure. This structure renders the upper transponder surface 12 carrying the idts 8, 10 responsive to the external pressure thereon.

The pressure difference between the reference chamber 16 and the region to be measured, to which the upper surface 12 of the device is exposed, will change the separation between the SAW's IDTs 8, 10 on the surface 12 at the two ends of the transponder 2. This change in separation will alter the group delay of a surface acoustic wave that is generated externally of the patient in whom the transponder 2 is implanted and which is picked up by the antenna 4 transmitted along the transponder surface 12 from the IDT 8 to the IDT 10 and reflected therefrom back to the IDT 8 and antenna 4.

An acoustic wave instigated at the IDT 8 by a stimulating radio frequency (RF) pulse received on the antenna 4 of the device 2 from source not shown external to the body of the portion will pass across the device 2 and be reflected back across the device 2 where the IDT 8 will transform the energy back to RF which will be transmitted by the antenna 4 to an external receiver. The time interval between the stimulating and transmitted RF pulses is used to measure the pressure.

An alternative arrangement is to have two antennae with the second antenna 4', shown in broken outline in FIG. 1, connected to the second IDT 10 of the transponder 2. A simulating RF pulse received at one of the antenna 4.4' is then transformed to a surface acoustic wave which will pass along the transponder 2 until it reaches the second IDT 10 where it will be transformed back to RF and be transmitted by the other of the antennae 4.4'. Again, the time interval between the stimulating and retransmitted pulses is used to measure the pressure.

Use as a Resonator:

With devices described as above, with one or two IDT structures and one or two antennae, the pressure difference between the reference chamber and the region to be measured varies the spacing of the fingers of the IDT structures 8, 10 and hence the natural frequency of the surface acoustic wave which will be generated by the reception of an RF pulse. Varying pressures will change the spacing between the SAW's interdigital fingers and hence alter the output frequency of the device 2. Other physical parameters such as temperature, fluid viscosity and even flow can alter the frequency as well and care must be used to make the sensor specific to pressure, that is to say, to eliminate unwanted effects of change other parameters on the output signal of the device 2.

The change in output frequency facilitates detection of the transmitted data to the external receiver system. In traditional systems such as RF ID tags equipped with sensing devices, the main obstacle to overcome is to distinguish between the data from the transponder and the reflections that occur naturally at any boundary of two tissue types. As the SAW device alters the output frequency, it can be easily distinguished from these natural reflections.

The external system consists of external antennae, orthogonally placed, which stimulate the implanted devices and receive the retransmitted signal. With both approaches, delay-line and resonator, the system can be made insensitive to other factors by using a pair of SAW devices—one sensitive to the desired measurement parameter and the other made insensitive by design and used as a reference to cancel the effects of unwanted parameters such as temperature variation and distance.

The present invention is applicable, for example, in the long term monitoring of the pressure-volume relationship of the left ventricle which provides critical information on cardiac function. Patients with implanted cardiac assist devices or transplanted hearts may be monitored continuously in the post-operative period and intermittently thereafter for as long as they live. Implanting biocompatibly-encapsulated SAW sensors at the time of the operation provides a simple and acceptable addition to the surgical procedure and can provide information that will assist in early diagnosis of subsequent impending heart failure with no need for any invasive (and therefore risky) procedures.

Cardiac monitoring, however, is only one application of the present invention. Another particularly important application is in the use of closed-loop control in cardiac assist devices where measurement of the instantaneous measurement of the pressure generated by the combination of natural heart activity and the assist device can be used to control the settings of the assist device to maintain good blood circulation in the patient.

The application described above is for SAW devices implanted within the cardiovascular system to monitor a single variable, pressure. It is also envisaged, however, that similar devices could be implanted elsewhere in the body to monitor, for example, intra-cranial pressure, pressure at locations within the gastro-intestinal tract or pressure within the bladder. The long-term accuracy of these devices leads to better-informed active patient management and patient care.

In other applications, SAW devices can be designed to be preferentially sensitive to other physical variables such as temperature, stress and torque, or to chemical concentrations of particular ions, for example oxygen, and pH values, compounds, for example carbon dioxide, or, when coated suitably, to particular compounds including proteins, for example glucose. A very large number of transducers is thus envisaged, all of which use the zero-power transponder modes of communication to the exterior described in the pressure application above.

Devices in accordance with the present invention could also be worn externally, rather than being implanted, if the desired physical or chemical variable can be measured there.

Furthermore, the SAW devices can be used for both monitoring and control functions in conjunction with other implanted systems, for example, cardiac pacemakers or cardiac-assist devices.

The devices described above are surface acoustic wave devices. However, it is also envisaged that bulk acoustic wave devices could alternatively be used for physiological monitoring, in which the acoustic wave propagates through the body of the device rather than along its surface.

The invention claimed is:

[1. A method of monitoring cardiovascular or intra-cranial pressure within a human or animal body comprising a surface acoustic wave device implanted therein, wherein the device comprises an interdigitated transducer on the surface of a piezo-electric substrate that closes a sealed chamber to form a transducer body, which substrate is exposed such that the cardiovascular or intra-cranial pressure to be monitored acts on the exposed substrate, wherein an antenna is connected to the interdigitated transducer, wherein a radio-frequency signal is supplied externally of the body to the antenna, is transmitted as a surface acoustic wave over the substrate surface to a reflector on the surface, reflected therefrom back to the said transducer and transmitted from the antenna to an external receiver, whereby comparison of the supplied and received signals provides a measurement of pressure difference across the substrate.]

[2. A method according to claim 1 wherein the cardiovascular or intra-cranial pressure is monitored by determination of a delay of the surface acoustic wave.]

[3. A method according to claim 1 wherein the cardiovascular or intra-cranial pressure is monitored by determination of the change of resonant frequency of the surface acoustic wave.]

[4. A method according to claim 1 wherein a plurality of said devices is employed arranged to operate at different frequencies.]

[5. A method of monitoring cardiovascular or intra-cranial pressure within a human or animal body, wherein a pair of surface acoustic wave devices is implanted in the body, a first of the devices being a pressure-sensitive acoustic wave device used in the method claimed in any one claim 1, 2, 3 or 4, and a second of the devices being a surface acoustic wave device which is relatively insensitive to the cardiovascular or intracranial pressure and being operated as a reference device thereby to cancel any effect on the cardiovascular or intracranial pressure measurement of unwanted parameters.]

[6. A method of monitoring cardiovascular or intra-cranial pressure within a human or animal body comprising an implanted surface acoustic wave device which comprises a pair of interdigitated transducers spaced apart over the surface of a piezoelectric substrate that seals over a chamber to form a transducer body, which substrate is exposed such that the cardiovascular or intra-cranial pressure to be monitored acts on the exposed substrate, wherein an antenna is connected to one of the interdigitated transducers, wherein a radio-frequency signal is supplied externally of the body to the antenna, is transmitted over the substrate surface as an acoustic wave to the other of the transducers, reflected therefrom back to the said one of the transducers and transmitted from the antenna thereof to an external receiver, whereby comparison of the supplied and received signals provides a measurement of the cardiovascular or intra-cranial pressure.]

*7. A cardiovascular or intra-cranial pressure monitoring system comprising:*

*a surface acoustic wave device,*

*a radio-frequency signal source for supplying a first radio-frequency signal to the surface acoustic wave device, and*

*a radio-frequency signal receiver for receiving a second radio-frequency signal from the surface acoustic wave device,*

*wherein the surface acoustic wave device comprises:*

*an interdigitated transducer on a surface of a piezoelectric substrate that closes a sealed chamber to form a transducer body,*

*a reflector on the surface of the substrate, and*

*an antenna connected to the interdigitated transducer,*

*which substrate is arranged to be exposed, in use, such that the cardiovascular or intra-cranial pressure to be monitored acts on the exposed substrate, and wherein the first radio-frequency signal transmitted by the radio-frequency signal source is arranged to be:*

*received by the antenna and transmitted as a surface acoustic wave over the substrate surface to the reflector,*

*reflected therefrom back to the said transducer, and*

*transmitted from the antenna to the radio-frequency signal receiver as the second radio-frequency signal, whereby comparison of the supplied and received signals provides a measurement of a pressure difference across the substrate together with at least one of map information and information downloaded by using a communication unit.*

*8. A cardiovascular or intra-cranial pressure monitoring system according to claim 7 wherein the cardiovascular or intra-cranial pressure is monitored by determination of a delay of the surface acoustic wave.*

*9. A cardiovascular or intra-cranial pressure monitoring system according to claim 7 wherein the cardiovascular or intra-cranial pressure is monitored by determination of the change of resonant frequency of the surface acoustic wave.*

*10. A cardiovascular or intra-cranial pressure monitoring system according to claim 7 wherein a plurality of said surface acoustic wave devices operate at different frequencies.*

*11. A cardiovascular or intra-cranial pressure monitoring system comprising a pair of surface acoustic wave devices, a first of the devices being a pressure-sensitive acoustic wave device as defined in claim 7 and a second of the devices being a surface acoustic wave device which is relatively insensitive to the cardiovascular or intra-cranial pressure and being operated as a reference device thereby to cancel any effect on the cardiovascular or intra-cranial pressure measurement of unwanted parameters.*

*12. A cardiovascular or intra-cranial pressure monitoring system comprising a pair of surface acoustic wave devices, a first of the devices being a pressure-sensitive acoustic wave device as defined in claim 8 and a second of the devices being a surface acoustic wave device which is relatively insensitive to the cardiovascular or intra-cranial pressure and being operated as a reference device thereby to cancel any effect on the cardiovascular or intra-cranial pressure measurement of unwanted parameters.*

* * * * *